United States Patent [19]

Fu et al.

[11] Patent Number: 5,569,797
[45] Date of Patent: Oct. 29, 1996

[54] METHOD OF REMOVING OLEFINIC IMPURITIES FROM HYDROCHLOROFLUOROCARBONS

[75] Inventors: Ta-Wei Fu, Newark; Velliyur N. M. Rao, Wilmington, both of Del.

[73] Assignee: E. I. Du Pont de Nemours and Company, Wilmington, Del.

[21] Appl. No.: 817,628

[22] Filed: Jan. 7, 1992

[51] Int. Cl.$^6$ ................................................. C07C 17/38
[52] U.S. Cl. ................................................. 570/177
[58] Field of Search ................................. 570/177

[56] References Cited

U.S. PATENT DOCUMENTS

| | | | |
|---|---|---|---|
| 2,942,036 | 6/1960 | Smith et al. | 260/653 |
| 3,439,052 | 4/1969 | Bjornosa | 260/653 |
| 3,505,417 | 4/1970 | Gardner | 260/653.5 |
| 3,636,172 | 1/1972 | Gardner | 260/635.5 |
| 4,129,603 | 12/1978 | Bell . | |
| 4,843,181 | 6/1989 | Gumprecht et al. | 570/169 |
| 5,001,287 | 3/1991 | Fernandez et al. | 570/178 |
| 5,105,035 | 4/1992 | Wang et al. | 570/178 |

FOREIGN PATENT DOCUMENTS

| | | |
|---|---|---|
| 0357328 | 3/1990 | European Pat. Off. ............ 570/177 |
| 0379793 | 8/1990 | European Pat. Off. . |
| 1149739 | 6/1989 | Japan . |
| 1578933 | 5/1977 | United Kingdom . |
| 9008750 | 8/1990 | WIPO ................................. 570/177 |

OTHER PUBLICATIONS

Chemistry of Organic Fluorine Compounds, 2nd (Revised) Edition "Reactions of Organic Fluorine Compounds", pp. 174–179 (1958).
"The Hydrogenation of Organic Fluorides And Chlorides", Lacher, et al. Trans. Faraday Soc. 52, 1500–1508 (1956).
Milos Hudlicky, "Chemistry of Organic Fluorine Compounds", John Wiley & Sons, 2nd Revised Ed., New York, p. 174, 1976.

*Primary Examiner*—Alan Siegel
*Attorney, Agent, or Firm*—Michael K. Boyer

[57] ABSTRACT

A process for preparing a hydrochlorofluorocarbon essentially free of olefinic impurities by selectively hydrogenating the olefinic impurities. The process may be controlled such that at least a portion of the hydrochlorofluorocarbon is converted into a fluorohydrocarbon.

14 Claims, No Drawings

METHOD OF REMOVING OLEFINIC IMPURITIES FROM HYDROCHLOROFLUOROCARBONS

FIELD OF THE INVENTION

The present invention relates to purifying a hydrochlorofluorocarbon which contains an olefinic impurity.

BACKGROUND OF THE INVENTION

Hydrochlorofluorocarbons are widely used as solvents, cleaning agents, blowing agents, and refrigerants. It is desirable that the hydrochlorofluorocarbon which is selected for such uses possess stability and freedom from toxic impurities. Olefinic impurities which are often present as impurities in the hydrochlorofluorocarbon may be toxic and/or unstable.

Hydrochlorofluorocarbons have been produced by methods such as the chlorination of fluorohydrocarbons, fluorination of hydrochlorocarbons, exchange reactions between hydrogen fluoride and hydrochlorocarbons, or the addition of chlorine, fluorine, hydrogen chloride, or hydrogen fluoride to halogenated olefins.

In several of these known methods, the resultant hydrochlorofluorocarbon typically contains at least traces of olefinic impurities even after fractional distillation.

Known methods for purifying hydrofluorocarbons containing olefinic impurities include reaction with aqueous potassium permanganate, amines, oxygen, sulfuric acid, or hydrogen fluoride. Each of these methods has significant disadvantages for hydrofluorocarbon purification such as requiring extensive operations, producing undesirable residues, and/or destroying undesirable amounts of the compound to be purified. These methods are at least as disadvantageous for purifying hydrochlorofluorocarbons because hydrochlorofluorocarbons are generally more subject to undesirable side reactions.

SUMMARY OF THE INVENTION

The present invention relates to a process for treating an impure mixture containing at least one hydrochlorofluorocarbon and at least one olefinic impurity by contacting the mixture with a source of hydrogen in the presence of a hydrogenation catalyst. During such contacting the olefinic impurity is converted to a hydrogenated form which is saturated. The treated mixture contains the hydrogenated form of the impurity, the original hydrochlorofluorocarbon(s), and optionally a hydrofluorocarbon which may be the hydrodechlorinated product of the original hydrochlorofluorocarbon. The hydrogenated form of the olefin is usually more stable and relatively non-toxic. The hydrogenated form of the olefin, which is now saturated, is generally a more acceptable impurity and the presence thereof may be permissible for certain end-use applications. However, if desired, purified hydrochlorofluorocarbon may be recovered by distilling the treated product or by other conventional separation methods thereby obtaining a product which is essentially free of the hydrogenated form of the olefin.

One aspect of the invention relates to a hydrogenation process for producing hydrochlorofluorocarbons, particularly those having 2 to 4 carbon atoms, which are essentially free of olefinic impurities. In this aspect of the invention, the hydrogenation process may be practiced such that the olefinic impurity is selectively hydrogenated. For example, a mixture containing a hydrochlorofluorocarbon and an olefinic impurity may be purified such that substantially only the olefinic impurity is hydrogenated.

The process of the invention may be controlled in a manner which permits co-producing, a hydrofluorocarbon product obtained by hydrodechlorination of a hydrochlorofluorocarbon wherein the olefinic impurities have also been hydrogenated. For example, the invention permits performing the hydrogenation process such that both the hydrochlorofluorocarbon and olefinic impurity are hydrogenated. This aspect of the invention produces a mixture containing the original hydrochlorofluorocarbon, a hydrofluorocarbon, i.e., hydrodechlorination product, and hydrogenated olefin.

DETAILED DESCRIPTION OF THE INVENTION

The present invention provides a solution to the problems associated with the presence of an olefinic impurity. The invention relates to hydrogenating the olefinic impurity by contacting an impure mixture comprising at least one hydrochlorofluorocarbon and at least one olefinic impurity with a hydrogenation catalyst, while in the presence of a hydrogen source. The contacted mixture comprises the hydrogenated form of the olefin, the original hydrochlorofluorocarbon, and optionally a hydrofluorocarbon such as a hydrodechlorination product of the original hydrochlorofluorocarbon. The contacted mixture is substantially free of the olefinic impurity.

By "hydrogenated form of the olefin" is meant a saturated compound wherein the olefinic linkage of the starting olefinic impurity is absent.

By "olefin" is meant an unsaturated impurity/impurities which are converted to the hydrogenated form of the olefin in accordance with the present invention.

By "substantially free" is meant a product or contacted mixture wherein greater than about 50% of the olefinic impurity has been converted to its hydrogenated form.

By "hydrochlorofluorocarbon" (HCFC) is meant an alkane in which the hydrogen atoms are incompletely replaced by fluorine and chlorine.

By "hydrofluorocarbon" (HFC) is meant an alkane in which the hydrogen atoms are incompletely replaced by fluorine.

By "perhalogenated compound" is meant an alkane wherein all the hydrogens are replaced by either fluorine and/or chlorine. Compounds containing bromine, which is substituted for one, two, or more of the chlorines, are expected to undergo similar chemistry.

A suitable HCFC comprises a compound having a structure corresponding to RCClXY, where R is a perfluoroalkyl or hydroperfluoroalkyl residue and X and Y are chosen from the group H, Cl, F, or R, but at least one of X and Y is H if R is perfluoroalkyl. Examples of suitable HCFC compounds are 1,1,1,2-tetrafluoro-2-chloroethane, 1,1,1-trifluoro-2,2-dichloroethane, 2-hydro-1-chloro-perfluoropropane, among others.

Examples of suitable HFC compounds are $CF_3CH_3$, $CF_3CH_2F$, $CF_3CHF_2$, $CF_2HCF_2H$, $CF_3CH_2CF_3$ and $CF_2HCH_3$ among others.

Representative olefinic impurities that can be hydrogenated and removed from the hydrochlorofluorocarbon include $CH_2=CH_2$, $CH_2=CHCl$, $CHCl=CHCl$, $CH_2=CC1_2$, $CHCl=CCl_2$, $CHF_2=CH_2, CF_2=CF_2$, $CHF_2=CF_2$, $CF_2=CCLF$, $CF_2=CClF$, $CH_2=CClF$, $CH_3=CF=CH_2$, $CF_3CF=CF_2$, $CF_3CH=CHCF_3$, (CF$_3$)$_2$C=CF$_2$, CClF$_2$CF$_2$CF=CF$_2$, CF$_3$CF=CHCF$_3$, CF$_3$CF=CFCF$_3$, CF$_3$CF=CF$_3$, CF$_3$CCl=CHCF$_3$ and CF$_3$CF=CHCF$_3$ among others. Typically, the olefinic impurities are produced as byproducts of the reactions which are used for producing the HCFC. Such olefinic impurities typically have sufficiently similar volatility to the HCFC that they are incompletely removed during isolation of the HCFC by conventional means such as distillation. One such olefinic impurity comprises the cis- and trans-perfluorobutene-2 isomers (FC-1318) which is typically formed when producing 1,1,1,2-tetrafluoro-2-chloroethane (HCFC-124).

The HCFCs which are purified by the present invention may be produced by any suitable process.

One suitable process for producing a HCFC comprises selectively reducing a chlorine atom in a perhaloalkane such as chlorofluorocarbon (CFC). In one aspect of this process, the reduction is performed by a hydrogenation reaction which is carried out in the presence of a group VIII metal catalyst, e.g., palladium, at a temperature which ranges from about 80° C.–300° C. In one case, the hydrogenation reaction provides a hydrogen containing chlorofluoroalkane (HCFC) represented by the general formula

R—CClXH wherein R represents trifluoromethyl group, chlorodifluoromethyl group, dichlorofluoromethyl group, chlorofluoromethyl group, difluoromethyl group, fluoromethyl group or 2-chloro-1,1,2,2-tetrafluoroethyl group, and X represents a chlorine atom or a fluorine atom and in which the perhaloalkane or halogenated alkane, which is hydrogenated, is represented by the general formula:

R—CCl$_2$X wherein R and X are as defined earlier. Suitable compounds for use in the process for producing the HCFC include one or more of CF$_3$—CCl$_3$, CF$_3$—CCl$_2$F, CF$_2$Cl—CCl$_3$, CF$_2$Cl—CCl$_2$F, CFCl$_2$—CCl$_2$F, ClCF$_2$CF$_2$CCl$_3$ among others.

The amount of hydrogen which is used for performing the reduction or hydrogenation which forms the HCFC ranges from about 0.5 to about 5.0 moles per one mole of the starting material, i.e., a halogenated alkane.

The reaction temperature and conversion ratio when producing the HCFC are inter-related, however, the reaction temperature should be about 80–300 C and normally about 100°–200° C. For best results, the HCFC formation reaction time ranges from one to about sixty seconds, normally five to thirty seconds.

A second suitable process for obtaining a HCFC, e.g., 1,1,1-trifluorodichloroethane, 1,1,1,2-tetrafluorochloroethane, among others, comprises fluorinating at least one of tetrahaloethylene, C$_2$Cl$_{4-x}$F$_x$, wherein x=0 to 3, and/or a pentahaloethane, C$_2$HCl$_{5-x}$F$_x$, wherein x=0 to 2. The fluorination process comprises contacting in the gaseous phase at effective temperature, mol ratio, and contact time, the tetrahaloethylene and/or pentahaloethane with HF and Cr$_2$O$_3$. Preferably, the Cr$_2$O$_3$ is prepared by pyrolyzing (NH$_4$)$_2$Cr$_2$O$_7$. This fluorination process produces a product stream containing 1,1,1-trifluorodichloroethane and/or 1,1,1,2-tetrafluorochloroethane and pentafluoroethane, wherein the amount of said 1,1,1-trifluorodichloroethane and/or 1,1,1,2-tetrafluorochloroethane is preferably greater than the amount of pentafluoroethane produced. Thereafter, the 1,1,1-trifluorodichloroethane and/or 1,1,1,2-tetrafluorochloroethane may be separated from the product stream.

The process for purifying a HCFC by removal of an olefinic impurity in accordance with the present invention is conducted by contacting, either batchwise or continuously, a substantially dry impure mixture containing an olefinic impurity, a HCFC and optionally HFC in gaseous or liquid form, and a hydrogen source with a hydrogenation catalyst, e.g. Pd/C, Pt/C, Rh/C and Re/C, among others. For example, a gaseous stream comprising an impure mixture and hydrogen is passed through a reactor which houses a particulate bed of the hydrogenation catalyst that is maintained at a desired temperature. The exiting stream, i.e. treated mixture, from the reactor contains a HCFC, optionally HFC, and an olefinic impurity in a hydrogenated form. If desired, the treated mixture can be treated further by conventional methods, e.g., fractional distillation, thereby removing hydrogen and acidic gases, if any, and separating the components from each other.

A significant quantity of the olefinic impurity in the HCFC can usually be removed by using standard physical means such as fractional distillation. As a result, the quantity of the olefinic impurities which remains to be treated by the method of this invention will generally be less than about 5% by weight of the HCFC, and normally ranges from about 0.5% down to about 0.003%. However, even this small amount of an olefinic impurity is typically undesirable, i.e., the olefinic impurity tends to be unstable and/or toxic. In most cases, the invention is effective in lowering the olefinic impurity content to below about 0.001%. In other words, the invention permits producing or purifying a hydrochlorofluorocarbon which has less than about 10 ppm of an olefinic impurity.

The hydrogenated form of the olefinic impurity is relatively more stable and usually non-toxic. As such, the presence of the hydrogenated form of the olefinic impurity may be permissible for certain end-use applications, i.e., a mixture containing the hydrochlorofluorocarbon and a hydrogenated olefin possesses utility, e.g., a refrigerant. However, if desired, the hydrogenated olefin can be removed and recovered by any suitable technique which does not adversely affect the characteristics of the hydrochlorofluorocarbon. One suitable technique comprises distilling, which substantially removes the hydrogenated olefin, thereby providing a HCFC that is substantially free of olefinic impurities and hydrogenated forms thereof.

It was a surprising discovery that the invention permits selectively hydrogenating the olefinic impurity while maintaining the original quantity of the HCFC. In other words, the HCFC is substantially not attacked or reduced during the hydrogenation process which reduces the olefinic impurities. For example, a mixture comprising a HCFC, optionally a HFC, and an olefinic impurity may be purified by selectively hydrogenating the olefin wherein the quantity of HCFC before and after the hydrogenation remains substantially constant.

Moreover, the invention permits controlling the hydrogenating process such that at least a portion of the HCFC is converted into a HFC. In contrast to the selective hydrogenation discussed above, this aspect of the invention may be used for coproducing a hydrogenated olefin, i.e., which purifies a mixture containing an olefinic impurity, and a HFC. For example, a mixture comprising a HCFC, optionally a HFC, and an olefinic impurity may be purified by hydrogenating the olefin and at least a portion of the HCFC to a HFC.

The invention, therefore, may be used for obtaining a mixture having a wide range of compositions which have been purified by hydrogenating an olefinic impurity. The compositions may range from a mixture consisting essentially of a HCFC and a hydrogenated olefin to a mixture comprising a HCFC, HFC, and a hydrogenated olefin. Further, the invention may be practiced by hydrogenating the olefinic impurity on-line while producing the HCFC and/or by purifying an existing HCFC mixture containing an olefinic impurity.

The temperature of the hydrogenating process may be used for controlling the selectivity of the process. By monitoring the temperature of the hydrogenation environment, the invention permits obtaining the wide range of compositions which were discussed above. For example, when purifying or producing a HCFC comprising HCFC-24 which contains an olefinic impurity comprising FC-1318, a hydrogenation temperature should be used which ranges from about 100°–200° C. Should it be desirable to selectively hydrogenate substantially only the olefinic impurity, a hydrogenation temperature should be used which ranges from about 100°–150° C. However, the specific temperature which is used for practicing the invention will vary depending upon at least one of the HCFC composition, degree to which the HCFC is to be hydrogenated, and olefinic impurity.

Any hydrogenation catalyst may be used for practicing the invention which substantially converts at least the olefin to a hydrogenated compound. Generally, a catalyst selected from one or more Group VIII metals, and rhenium is suitable. In some cases it may be desirable to alloy the Group VIII metal catalyst with one or more Group IB metals. The catalyst can be supported or unsupported. Suitable support materials comprise at least one member from the group of carbon, aluminum oxide, silicon carbide, aluminum fluoride and calcium fluoride among others.

Hydrogen can be fed either in the substantially pure state or diluted with a carrier which is inert to the process. Suitable inert carriers comprise at least one gas from the group of nitrogen, helium, argon among others.

While a vapor phase reaction is typically expedient, the hydrogenation reaction may be performed in the liquid phase. Contact time, mole ratio of hydrogen to organic compounds, and pressure may be controlled depending on the degree of hydrogenation desired. The molar ratio of hydrogen to hydrochlorofluorocarbon can vary widely. Generally, the molar ratio ranges from about 0.1 to about 5.0. When hydrogenating or removing an olefinic impurity comprising FC-1318 from a hydrochlorofluorocarbon such as HCFC-124, it is preferable to use a molar ratio which ranges from about 0.5 to about 2.0.

The pressure which is used for practicing the invention is not a critical aspect of the invention. Atmospheric and superatmospheric pressures tend to be expedient, and therefore, are preferred.

The following Examples are provided to illustrate and not limit the scope of the invention defined in the appended claims. Unless specified otherwise, commercially available and substantially pure materials were used when performing the following Examples.

EXAMPLES

In Examples 1–3, 1,1,1,2-tetrafluoroethane (HFC-134a) was coproduced during the purification of 1,1,1,2-tetrafluoro-2-chloroethane (HCFC124), thereby removing perfluorobutene (olefin) impurities. As a result, the olefinic impurity was substantially or completely removed and a portion of the hydrochlorofluorocarbon was converted to a fluorohydrocarbon. Example 4 demonstrates that removal of the olefinic material can also be accomplished with negligible conversion of the original hydrochlorofluorocarbon.

The organic products were separated by gas-liquid chromatography using a column containing "Krytox" ("Krytox" is a registered trademark of the Du Pont Company for a perfluoropolyether liquid), on an inert support. The products were detected by flame ionization and calculated as a mole percentage of the organic material. Unless stated otherwise the percentages are reported in mole %.

EXAMPLE 1

A tubular reactor about 10 feet in length and about 1 inch in diameter was packed with 4 to 8 mesh catalyst containing about 0.5% palladium on carbon, and heated in an oil bath to about 288° C. A sample of 1,1,1,2-tetrafluoro-2-chloroethane containing about 39 ppm of the olefin FC-1318 was mixed with about 0.6 moles of hydrogen per mole of HCFC. The sample was passed through the reactor at about 50 psig at a rate of about 0.50 grams of organics per gram of catalyst per hour. The reaction product exiting the tube contained no detectable perfluorobutenes (i.e., the reaction product contained less than about 10 ppm of FC-1318). About 38% of the starting material was converted to 1,1,1,2-tetrafluoroethane (HFC-134a) and about 2% to 1,1,1-trifluoroethane (HFC-143a).

EXAMPLE 2

Example 2 was conducted under substantially the same conditions as Example 1, with the exception that the bath temperature was about 277° C. About 31% conversion to the tetrafluoroethane (HFC-134a) and 1.1% conversion to trifluoroethane (HFC-143a) was observed with no detectable perfluorobutene (FC-1318) in the product.

EXAMPLE 3

Example 3 was conducted under substantially the same conditions as Example 1, with the exception that the bath temperature was about 238° C. and the amount of FC-1318 present in the HCFC-124 was about 79 ppm. About 10% conversion to the tetrafluoroethane (HFC-134a) and 0.2% conversion to the trifluoroethane (HFC-143a) was observed. The reaction product was neutralized to remove the acids including HCl and HF, which was followed by distillation to isolate the HCFC-124. No perfluorobutene (FC-1318) was detected in the isolated HCFC-124.

EXAMPLE 4

In Example 4, the olefinic impurity was selectively hydrogenated while substantially maintaining the original quantity of the hydrochlorofluorocarbon. As a result, the olefinic impurity hydrogenated without substantial conversion of the original hydrochlorofluorocarbon to the hydrofluorocarbon.

An approximately 6" long X 0.5" I.D. nickel alloy reactor tube was charged with about 5.0 g of 0.5 % palladium on 4 to 8 mesh carbon particles. The charged reactor was placed in a sandbath and flushed with nitrogen. The charged reactor was then gradually heated to about 275° C. while dried hydrogen (20 cc/min) was passed through the reactor. The reactor was maintained at this temperature for an additional 12 hours. The reactor was then cooled under hydrogen to the desired operating temperature.

(A). The previously discussed reactor was heated to and maintained at about 100° C. The reactor was fed an impure mixture containing about 98.64% HCFC-124 and about 1.33% of a cis/trans mixture of FC-1318, and hydrogen. The mixture and hydrogen feed rates were about 10 cc/min. The product exiting the reactor was analyzed on line by using a gas chromatograph which was coupled to a mass spectrometer. After about 24 hours of operation, product analysis indicated the presence of about 98.63% by area HCFC-124 and about 1.35% HCFC-338mee ($CF_3CHFCHFCF_3$) which is the hydrogenated form of FC-1318. Substantially none of the starting olefin impurity was detected (i.e., less than about 10 ppm) in the exiting product stream. The amount of HCFC-124 converted to HFC-134a was less than about 0.02%.

(B). The process of item (A) above, was substantially repeated, except that the reactor was maintained at about 125° C. After about six hours of operation substantially no unconverted FC-1318 was observed. Only HCFC-338mee was detected, and the conversion of HCFC-124 to HFC-134a was less than about 0.1%.

While certain aspects of the invention have been described above in detail, an artisan in this art will readily recognize that other embodiments and variations are contemplated by the appended claims.

The following is claimed:

1. A process for removing an olefinic impurity from a mixture comprising a hydrochlorofluorocarbon wherein said hydrochlorofluorocarbon comprises at least one compound having a structure corresponding to RCClXY, wherein R is a perfluoroalkyl or hydroperfluoroalkyl, and X and Y comprise at least one member from the group of H, Cl, and F, said process comprising:

contacting said mixture with a source of hydrogen in the presence of a hydrogenation catalyst, whereby said contacting selectively hydrogenates substantially only said olefinic impurity, and recovering a mixture in which the olefinic impurity has been substantially removed.

2. The process of claim 1 further comprising converting at least a portion of said hydrochlorofluorocarbon to a hydrofluorocarbon.

3. The process of claim 2 wherein said hydrochlorofluorocarbon comprises HCFC-124 and said hydrofluorocarbon comprises HFC-134a.

4. A process for producing a hydrochlorofluorocarbon, said process comprising:

producing a hydrochlorofluorocarbon by at least one process selected from the group consisting of hydrogenating a haloalkane, and fluorinating a haloalkane, wherein said hydrochlorofluorocarbon is contaminated with an olefinic impurity and wherein said hydrochlorofluorocarbon comprises at least one compound having a structure corresponding RCClXY wherein R is a perfluoroalkyl or hydroperfluoroalkyl, and X and Y comprise at least one member from the group of H,Cl, and F, removing said olefinic impurity from said hydrochlorofluorocarbon by hydrogenating said olefin with a source of hydrogen while in the presence of a hydrogenation catalyst, wherein said removing selectively hydrogenates substantially only said impurity, and recovering a mixture comprising said hydrochlorofluorocarbon and a hydrogenated olefin.

5. The process of claim 1 wherein said hydrogenation is performed at a temperature from about 100° to about 200° C.

6. The process of claim 4 wherein said removing is performed at a temperature from about 100° to about 200° C.

7. The process of claim 1 wherein said catalyst comprises at least one member selected from the group consisting of palladium, platinum, group VIII metals, their alloys, and rhenium.

8. The process of claim 4 wherein said catalyst comprises at least one member selected from the group consisting of palladium, platinum, group VIII metals, their alloys, and rhenium.

9. The process of claim 1 wherein said olefin comprises at least one member of the group consisting of $CF_3CCl{=}CClCF_3$, $CF_3CF{=}CFCF_3$, $CF_3CF{=}CHCF_3$, $CF_3CCl{=}CHCF_3$, and $CF_3CH{=}CHCF_3$.

10. The process of claim 4 wherein said olefin comprises at least one member of the group consisting of $CF_3CCl{=}CClCF_3$, $CF_3CF{=}CFCF_3$, $CF_3CF{=}CHCF_3$, $CF_3CCl{=}CHCF_3$, and $CF_3CH{=}CHCF_3$.

11. The process of claim 1 further comprising coproducing a mixture including HFC-134a.

12. The process of claim 4 further comprising coproducing a mixture including HFC-134a.

13. A process for producing a hydrochlorofluorocarbon which is substantially free from olefinic impurities, said process comprising:

contacting a mixture, which comprises an olefin and a hydrochlorofluorocarbon, with a source of hydrogen in the presence of a hydrogenation catalyst, whereby the olefin is substantially hydrogenated, wherein said hydrochlorofluorocarbon comprises at least one compound having a structure corresponding to RCClXY, wherein R is a perfluoroalkyl or hydroperfluoroalkyl, and X and Y comprise at least one member from the group of H, Cl, and F, controlling the selectivity of the process by monitoring the temperature during said contacting, wherein said contacting selectively hydrogenates substantially only said olefinic impurity, and recovering said hydrochlorofluorocarbon.

14. The process of claim 13, further comprising converting at least a portion of said hydrochlorofluorocarbon into a hydrofluorocarbon.

* * * * *